United States Patent
Fix et al.

(10) Patent No.: US 9,816,920 B2
(45) Date of Patent: Nov. 14, 2017

(54) METHOD FOR PRODUCING AN INTEGRATED MICROMECHANICAL FLUID SENSOR COMPONENT, INTEGRATED MICROMECHANICAL FLUID SENSOR COMPONENT AND METHOD FOR DETECTING A FLUID BY MEANS OF AN INTEGRATED MICROMECHANICAL FLUID SENSOR COMPONENT

(71) Applicant: Robert Bosch GmbH, Stuttgart (DE)

(72) Inventors: Richard Fix, Weil Im Schoenbuch (DE); Rene Hartke, Aranjuez (ES); Jochen Beintner, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 15/112,163

(22) PCT Filed: Nov. 21, 2014

(86) PCT No.: PCT/EP2014/075242
§ 371 (c)(1),
(2) Date: Jul. 15, 2016

(87) PCT Pub. No.: WO2015/106861
PCT Pub. Date: Jul. 23, 2015

(65) Prior Publication Data
US 2016/0334329 A1  Nov. 17, 2016

(30) Foreign Application Priority Data

Jan. 15, 2014 (DE) .................. 10 2014 200 583

(51) Int. Cl.
*G01N 1/10* (2006.01)
*G01N 21/3504* (2014.01)
(Continued)

(52) U.S. Cl.
CPC ....... *G01N 21/3504* (2013.01); *G01N 21/359* (2013.01); *G01N 21/39* (2013.01);
(Continued)

(58) Field of Classification Search
CPC .............. G01N 21/39; G01N 21/3504; G01N 2021/451; H01S 5/0215; H01S 5/14
(Continued)

(56) References Cited

U.S. PATENT DOCUMENTS 5,852,308 A    12/1998  Wood
5,869,749 A     2/1999  Bonne et al.
(Continued)

FOREIGN PATENT DOCUMENTS

CN    203259470 U    10/2013
DE    600 02 387 T2   2/2004
(Continued)

OTHER PUBLICATIONS

International Search Report corresponding to PCT Application No. PCT/EP2014/075242, dated Feb. 27, 2015 (German and English language document) (6 pages).

*Primary Examiner* — Hoa Pham
(74) *Attorney, Agent, or Firm* — Maginot, Moore & Beck LLP (57) ABSTRACT

A method for producing an integrated micromechanical fluid sensor component includes forming a first wafer with a first Bragg reflector and with a light-emitting device on a first substrate. The light-emitting device is configured to emit light rays in an emission direction from a surface of the light-emitting device facing away from the first Bragg reflector. The method further includes forming a second wafer with a second Bragg reflector and with a photodiode on a second substrate. The photodiode is arranged on a surface of the second Bragg reflector facing towards the
(Continued)

second substrate. The method also includes bonding or gluing the first wafer to the second wafer such that there is formed a cavity into which a fluid is introduced and through which the light rays can pass. The method further includes separating the fluid sensor component from the first and the second wafer.

8 Claims, 6 Drawing Sheets

(51) Int. Cl.
| | | |
|---|---|---|
| *G01N 21/359* | (2014.01) | |
| *G01N 21/39* | (2006.01) | |
| *H01S 5/00* | (2006.01) | |
| *H01S 5/026* | (2006.01) | |
| *H01S 5/06* | (2006.01) | |
| *H01S 5/183* | (2006.01) | |

(52) U.S. Cl.
CPC .......... *H01S 5/0028* (2013.01); *H01S 5/0264* (2013.01); *H01S 5/0607* (2013.01); *H01S 5/18361* (2013.01); *G01N 2201/0612* (2013.01); *H01S 5/18363* (2013.01)

(58) Field of Classification Search
USPC .......... 356/246, 432–440; 372/50.124, 50.12; 257/14
See application file for complete search history.

(56) References Cited

U.S. PATENT DOCUMENTS

| | | | |
|---|---|---|---|
| 7,307,271 B2* | 12/2007 | Islam | B82Y 10/00 257/14 |
| 7,400,665 B2* | 7/2008 | Wang | B82Y 10/00 372/50.12 |
| 2004/0223881 A1 | 11/2004 | Cunningham et al. | |
| 2005/0157301 A1 | 7/2005 | Chediak et al. | |
| 2009/0303487 A1 | 12/2009 | Bond et al. | |
| 2011/0184624 A1 | 7/2011 | Han et al. | |
| 2013/0193003 A1 | 8/2013 | Reed et al. | |

FOREIGN PATENT DOCUMENTS

| | | |
|---|---|---|
| DE | 103 18 767 A1 | 12/2004 |
| JP | 2000-261096 A | 9/2000 |
| JP | 2003-57438 A | 2/2003 |
| JP | 2011-527750 A | 11/2011 |
| WO | 2005/026705 A1 | 3/2005 |

\* cited by examiner

METHOD FOR PRODUCING AN INTEGRATED MICROMECHANICAL FLUID SENSOR COMPONENT, INTEGRATED MICROMECHANICAL FLUID SENSOR COMPONENT AND METHOD FOR DETECTING A FLUID BY MEANS OF AN INTEGRATED MICROMECHANICAL FLUID SENSOR COMPONENT

This application is a 35 U.S.C. §371 National Stage Application of PCT/EP2014/075242, filed on Nov. 21, 2014, which claims the benefit of priority to Serial No. DE 10 2014 200 583.3, filed on Jan. 15, 2014 in Germany, the disclosures of which are incorporated herein by reference in their entirety.

BACKGROUND

The present disclosure relates to a method for producing an integrated micromechanical fluid sensor component, to an integrated micromechanical fluid sensor component and to a method for detecting a fluid by means of an integrated micromechanical fluid sensor component. The fluid may, in particular, be a gas or a gas mixture. During the detection, a molecular concentration of the fluid, or in the fluid, or a type of fluid may in particular be determinable.

Optical spectroscopy for the detection of constituents (analytes) of a fluid, for instance of a gas mixture, is based on the interaction of the analytes with photons. A structure consisting of a light emission device, for instance an LED or a laser diode, a detector, for instance a photodiode or a thermopile, and an optical measurement path is conventionally used for the measurement. The optical measurement path extends at least partially through the fluid to be analyzed, or the fluid to be analyzed is introduced into the measurement path. This may, for example, be done actively by forming a flow or passively by allowing convection or diffusion. Signals of the detector are read out in order to be able to draw conclusions about, for instance, a type of fluid or a molecular concentration. In this case, use is made of the fact that the emitted light is partially absorbed by the fluid to be analyzed and/or the analyte.

WO 2005/026705 A1 describes a gas detection method and a gas detection apparatus. The gas detector apparatus comprises a surface emitter, VCSEL, a test chamber and a light sensor. The light sensor detects light rays emitted by the surface emitter, which have passed through a gas to be detected in the test chamber. By means of connected electronics, signals generated by the light sensor are evaluated.

In so-called intracavity laser absorption spectroscopy, ICLAS, use is made of the fact that light makes a very large number of passes through an optical resonator. Since the sensitivity of the sensors depends on the optical path length in the medium, an extremely high sensitivity can be achieved with ICLAS methods.

SUMMARY

The present disclosure discloses a method for producing an integrated micromechanical fluid sensor component, an integrated micromechanical fluid sensor component having the features of patent claim 9, and a method for measuring a molecular concentration in a fluid by means of an integrated micromechanical fluid sensor component.

Accordingly, a method for producing an integrated micromechanical fluid sensor component is provided, having the steps of:

forming a first wafer having a first Bragg mirror and a light emission device on a first substrate, the light emission device being configured in order to emit light rays from a surface, facing away from the first Bragg mirror, of the light emission device in an emission direction;

wherein the first Bragg mirror and the light emission device are formed on a first surface of the first substrate, wherein the emission direction is perpendicular to the first surface of the first substrate, and wherein the light emission device and the first Bragg mirror are configured in such a way that emitted light rays traveling counter to the emission direction and striking the first Bragg mirror can be reflected in a first percentage in the direction of the emission direction;

forming a second wafer having a second Bragg mirror and a photodiode on a second substrate, the photodiode being arranged on a surface, facing toward the second substrate, of the second Bragg mirror;

bonding or adhesively bonding the first wafer onto the second wafer in such a way that, on the side, facing away from the first Bragg mirror, of the light emission device and on a surface, facing away from the photodiode, of the second Bragg mirror, a cavity, into which a fluid can be introduced and which can be passed through by the light rays, is formed;

wherein the light emission device and the second Bragg mirror are configured and arranged in such a way that the emitted light rays traveling in the direction of the emission direction and striking the second Bragg mirror can be reflected in a second percentage counter to the emission direction and can be transmitted in a further percentage;

wherein the photodiode is configured and arranged in such a way that at least some of the light rays strike the photodiode, after passing through the cavity and after transmission of the light rays through the second Bragg mirror; and dividing up the fluid sensor component from the first and second wafers.

If a first element is intended to be formed "on" a surface of a second element, this is intended to mean both that it is formed directly on the second element on the surface, and that it is formed over or under this surface, depending on the perspective. If the first element is intended to be formed "at" the surface of the second element, this is intended to mean that it is formed directly on the surface. If the first element is intended to be arranged in a particular way in relation to a second element, this is not necessarily intended to mean that the second element must already have been formed when the first element is formed. Rather, it describes a final state which the person skilled in the art knows how to produce according to the description.

The light emission device may in particular comprise a quantum well or a cavity, or consist thereof.

The cavity lies inside the optical resonator which is formed in the fluid sensor component by the light emission device and the Bragg mirrors. Because of the presence of a fluid in the cavity, the optical properties of the resonator (ICLAS) are changed. These changes may be determined by measuring a signal of the photodiode, in particular a light intensity signal, for instance a power or voltage in the case in which the light emission device is supplied with a known current. In this way, conclusions are possible regarding, for example, a molecular concentration of a molecule to be detected of the fluid, or in the fluid, or a type of fluid. Advantageously, the cavity is higher than 2 µm in a direction parallel to the emission direction. Exchange of the fluid in the cavity with the surroundings can be improved in this way.

A method for detecting a fluid by means of an integrated micromechanical fluid sensor component according to the disclosure is furthermore provided, having the steps of: recording a P-I characteristic curve while the fluid is in the cavity, a current I being a current with which the light emission device is supplied in order to emit the light rays, and a power P being a power which is formed on the photodiode in response to the light rays striking the photodiode on the photodiode and is read out from the photodiode; determining a threshold current, which is a value of the current I at which the power P on the photodiode assumes a finite value according to the P-I characteristic curve; comparing the determined threshold current with a predetermined reference threshold current for detection of the fluid.

The discovery on which the present disclosure is based is that there is a need for fluid sensors having an extremely compact design and technically simpler production.

The idea on which the present disclosure is based is now to take this discovery into account and to provide a method for producing integrated micromechanical fluid sensor components on the wafer scale. That is to say, entire wafers are processed and the fluid sensor components are then divided up.

By the production method according to the disclosure, an extremely compact design of the fluid sensor component, for example less than 10×10×10 mm3, in particular less than 1×1×1 mm3, can be made possible. A sensitivity of the fluid sensor component may be better than 1000 ppm, in particular better than 1 ppm. By production on the wafer scale, a high scaling effect is possible, and for example several thousand fluid sensor components may be producible simultaneously. In this case, the particularly compact structure of the fluid sensor component as a mesa is advantageous. The fluid sensor components and/or individual parts, for example the laser emission device, are advantageously already testable on the wafer. After the fluid sensor components have been divided up, further adjustment may be unnecessary.

The apparatus according to the disclosure can be optimized in a versatile way for different constraints, for example a low temperature dependency, a high or low sensitivity, a low threshold current, a low power consumption and/or a measurement speed.

Because of the monolithic integrated design, the fluid sensor component is particularly robust in respect of accelerations or vibrations.

The fluid sensor component according to the disclosure can have a particularly low power consumption, for example a power consumption of less than 10 mW, in particular less than 1 mW. Only a low current I may also be necessary, so that the fluid sensor component also produces only little waste heat.

The fluid sensor component according to the disclosure can be adjusted by means of the production method according to the disclosure to many different wavelengths on the basis of the known surface emitter (VCSEL) technology, and can therefore be used for a multiplicity of fluids, for instance gases. For example, it may be configured with a wavelength of 2 µm for measuring a molecular concentration of $CO_2$.

The fluid sensor component according to the disclosure can, for example, but not only, be usable in consumer articles such as cellphones, in the household, as a gas alarm, in medical technology equipment, for example for breath analysis or for lab-on-a-chip analysis systems and/or for use in liquids, for example for fuel analysis or for the analysis of bodily fluids. Hybrid applications are also possible, for example use as an alcohol breath tester on a cellphone. Because of the small overall size, implantation of the fluid sensor component with a micromechanical semiconductor control apparatus in a human body is, for example, also conceivable.

Advantageous embodiments and refinements are found in the dependent claims and in the description with reference to the figures.

According to one preferred refinement, the laser emission device is arranged between the first Bragg mirror and the first substrate. Furthermore, the bonding or adhesive bonding of the second wafer onto the first wafer is carried out by bonding the second Bragg mirror onto the first substrate, and the first substrate is structured in such a way that the cavity is formed in the first substrate. In this way, an additional spacer device is not required, which can further reduce the technical outlay and the spatial dimensions of the fluid sensor component.

According to another preferred refinement, the first Bragg mirror is arranged between the first substrate and the light emission device. The bonding or adhesive bonding of the first wafer onto the second wafer is carried out by means of a spacer device, and the cavity is defined by the spacer device. In this way, the fluid sensor component can be adapted in a versatile way to different fields of use. A technical outlay can also be reduced.

According to another preferred refinement, the spacer device is formed by the steps of: processing first contact pads on the first wafer;

processing second contact pads on the second wafer; processing metal columns on the first or second contact pads; and bonding the metal columns to the second or first contact pads in order to bond the first wafer onto the second wafer.

According to another preferred refinement, the spacer device is formed by the steps of: applying a sacrificial layer onto the first or second wafer; structuring the sacrificial layer; applying a conductive layer; structuring the conductive layer; and removing the sacrificial layer after the bonding or adhesive bonding of the second wafer onto the first wafer by means of the spacer device.

According to another preferred refinement, the photodiode is arranged between the second substrate and the second Bragg reflector.

According to another preferred refinement, the second substrate is a substrate which is essentially transparent for the light rays and is arranged between the second Bragg reflector and the photodiode.

According to another preferred refinement, a third Bragg mirror as a constituent of the first wafer is formed on the surface, facing away from the first Bragg mirror, of the light emission device. The light emission device and the third Bragg mirror are configured in such a way that the emitted light rays traveling in the direction of the emission direction and striking the third Bragg mirror can be reflected in a third percentage counter to the emission direction and can be transmitted in yet another percentage. By using the third Bragg mirror, a threshold current or threshold of the surface emitter or of the optical resonator can be reduced.

BRIEF DESCRIPTION OF THE DRAWINGS

The present disclosure will be explained in more detail below with the aid of the exemplary embodiments represented in the schematic figures of the drawings, in which.

In all the figures, unless otherwise indicated, elements and apparatuses which are the same or functionally equivalent are provided with the same reference signs.

DETAILED DESCRIPTION

Figure 1:
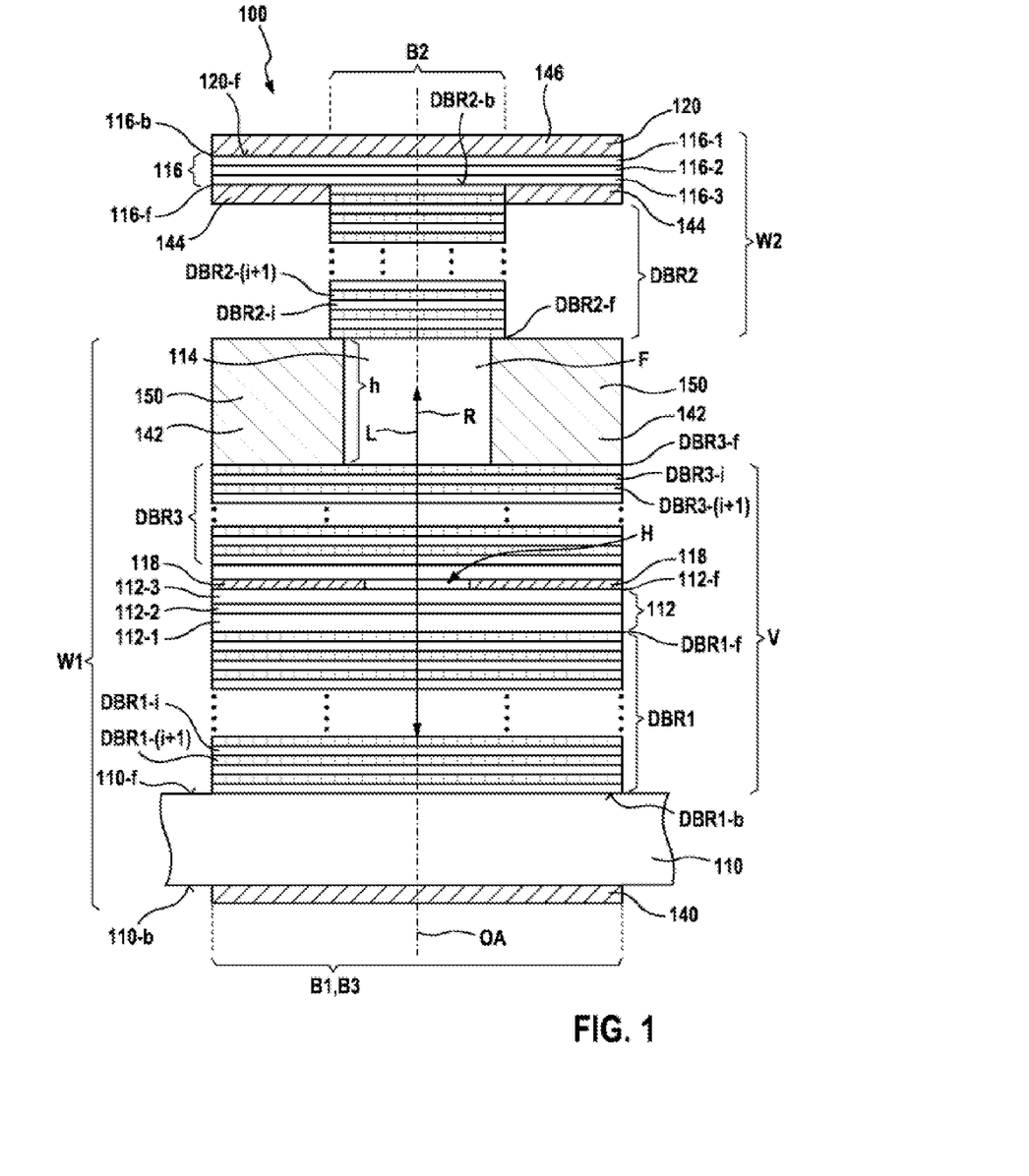
FIG. 1 shows a schematic cross section through a fluid sensor component according to a first embodiment of the present disclosure.

FIG. 1 shows a schematic cross section through a fluid sensor component 100 according to a first embodiment of the present disclosure.

A production method according to the disclosure for producing the fluid sensor component 100 will also be explained below with the aid of FIG. 1. FIG. 1 is not true to scale, and protective layers are not represented.

A first substrate 110 is provided as part of a first wafer W1, for example a flat silicon wafer. The first substrate 110 may be metallic or consist of heavily doped silicon, so that it is conductive. The first substrate 110 has a first surface 110-$f$ and a second surface 110-$b$, which lie essentially parallel to one another. According to the first embodiment, a first Bragg mirror DBR1 is grown epitaxially at the first surface 110-$f$ of the first substrate 110. Bragg mirrors are efficient reflectors, which consist of alternating first and second thin films DBR1-$i$, DBR1-(i+1) with different refractive indices. By way of example, a multiplicity of such pairs of thin films DBR1-$i$ are indicated in FIG. 1. As indicated by the dots in FIG. 1, however, layers DBR-$i$ in a number larger or smaller than that shown are also possible. The number of layers DBR-$i$ and the refractive indices of the layers may be selected according to the properties of a light ray to be reflected. In particular, the Bragg mirror may be a high-quality reflector when a wavelength of the light rays to be reflected lies close to the multiple of an effective optical length of the layers DBR-$i$, since light rays reflected at the layers DBR-$i$ interfere constructively.

According to the first embodiment, the first Bragg mirror DBR1 is configured in such a way that light rays striking (or entering) the first Bragg mirror DBR1 in the direction of the first substrate 110 are reflected strongly from the first surface 110-$f$ of the first substrate 110. The first Bragg mirror DBR1 has a first surface DBR1-$f$ and a second surface DBR1-$b$, which are essentially parallel to one another and face away from one another. The first Bragg mirror DBR1 is grown starting with the second surface DBR1-$b$ onto the first surface 110-$f$ of the first substrate 110.

A light emission device 112 is grown epitaxially on, advantageously at, the surface DBR1-$f$ which faces away from the first surface 110-$f$. The light emission device 112 is configured according to the first embodiment as a quantum well having three layers 112-1, 112-2, 112-3. The light emission device 112 is configured in order to emit light rays from a side 112-$f$, facing away from the first Bragg mirror DBR1, of the light emission device 112 in an emission direction R. The light emission device 112 and the first Bragg mirror DBR1 are configured in such a way that light rays L traveling counter to the emission direction R and striking the first Bragg mirror DBR1 can be reflected in a first percentage in the direction of the emission direction R. The first percentage may for example lie between 99% and 100%, advantageously between 99.8% and 100%, in particular between 99.9% and 100%.

According to the first embodiment, a current aperture 118 is formed on the surface 112-$f$ facing away from the first Bragg mirror DBR1. The current aperture 118 consists of a structured oxide layer into which an internally lying opening H is structured, for example by etching. In particular, the opening H is arranged symmetrically with respect to an optical axis OA of the fluid sensor component 100. The optical axis OA is arranged parallel to the emission direction R and perpendicularly to the surfaces 110-$b$, 110-$f$, DBR1-$b$, DBR1-$f$ and 112-$f$. The current aperture may be used so that a particular region of the quantum well in the vicinity of the opening H can be powered as uniformly as possible. Particularly uniform current strength can therefore be formed in this region, which is greater in this region compared with other regions of the light emission device 112. Light emission of the light emission device 112 can therefore take place to an increased extent in the region of the opening H.

On a surface of the current aperture 118 facing away from the light emission device 112, a further Bragg mirror DBR3 is formed, which will be referred to below as the third Bragg mirror DBR3. The third Bragg mirror DBR3 and the light emission device 112 are configured in such a way that light rays L traveling in the direction of the emission direction R and striking the third Bragg mirror DBR3 can be reflected in a third percentage counter to the emission direction R. The third percentage may for example lie between 95% and 100%, in particular between 96% and 99%, more particularly between 98% and 99%. In particular, the third percentage is advantageously less than the second percentage. Furthermore, the light rays L are transmitted through the third Bragg mirror DBR3 in a further percentage. The further percentage is significantly less than the third percentage, and may in particular be the remainder of subtraction of the third percentage from the number one.

With the first Bragg mirror DBR1, the light emission device 112 and the third Bragg mirror DBR3, an optical resonator is therefore already formed. Since the light rays L are emitted perpendicularly to the surface 110-$f$ of the first substrate 110, the parts of first substrate 110, first Bragg mirror DBR1, laser emission device 112, current aperture 118 and third Bragg mirror DBR3 may be referred to as a surface emitter V (or VCSEL for vertical-cavity surface-emitting laser).

A first electrical contact 140 may be formed as a structured metal layer at the second surface 110-$b$ of the first substrate 110. According to the first embodiment, a second electrical contact 142 is also formed as a structured metal layer at a side DBR3-$f$ of the third Bragg mirror DBR3 facing away from the light emission device 112. The second electrical contact 142 is configured with a cavity 114 in such a way that the light rays L can pass fully through the structured metal layer of the second electrical contact 142 inside the cavity 114 in a direction parallel to the emission direction R. The optical axis OA likewise extends fully inside the second electrical contact inside the cavity 114. Furthermore, the second contact 142 is structured in such a way that a fluid F can be introduced from an outer side of the fluid sensor component 100 into the cavity 114. The surface emitter V can be electrically pumped via the first and second electrical contacts 140, 142. To this end, a drive apparatus which comprises power electronics may be used.

Advantageously, a multiplicity of surface emitters V, respectively having corresponding first and second electrical contacts 140, 142, may be formed on the first substrate 110. This gives a first wafer W1 having the multiplicity of surface emitters V, which are configured in the form of mesas on the first substrate 110.

In order to produce a second wafer W2, an active zone of a photodiode 116 is applied on a second substrate 120. In this case, a first surface 116-b of the photodiode lies at a first surface 120-f of the second substrate 120. The second substrate 120 is preferably n-doped. In order to avoid growth defects and for substrate matching, a buffer layer may optionally be applied between the second substrate 120 and the photodiode 116. The active zone of the photodiode 116 preferably consists of an n-doped layer 116-1 applied on the second substrate 120 or the buffer layer, and a p-doped layer 116-3, which is as thin as possible, applied thereon. A large proportion of the light rays L can therefore reach the p-n junction. According to the first embodiment, an optional intrinsic layer 116-2 is deposited between the p- and n-doped layers 116-3, 116-11. In this way, the reverse voltage can be increased and/or the barrier layer capacitance can be reduced. Conventional materials for the active zone are Si (in particular for the wavelength range of up to 1.1 μm), Ge (in particular for the wavelength range of up to 1.8 μm) as well as GeAu, GaAs, InGaAs or CdTe.

According to the first embodiment, a second Bragg mirror DBR2 having a second surface DBR2-b of the second Bragg mirror DBR2 is formed on a second surface 116-f of the photodiode 116, facing away from the second substrate 120, which is in particular a surface of the p-doped layer 116-3. Around the second Bragg mirror DBR2, which is nonconductive, a third electrical contact 144 is formed on the second surface 116-f of the photodiode. Via the third electrical contact 144 and the electrically conductive second substrate 120 as a fourth electrical contact 146, a voltage U applied to the photodiode 116, in particular because of the light rays L incident on the photodiode 116, can be read out.

The light emission device 112 and the second Bragg mirror DBR2 are configured in such a way that light rays L striking the second Bragg mirror DBR2 in the direction of the photodiode 116 can be reflected in a second percentage in an opposite direction. The second percentage may for example lie between 99% and 100%, advantageously between 99.8% and 100%, in particular between 99.9% and 100%. In particular, the second percentage is advantageously greater than the third percentage.

The first, second and third Bragg mirrors DBR1, DBR2, DBR3 may respectively comprise different dielectric layers DBR1-i, DBR2-i, DBR3-i having respectively different thicknesses. The precise configuration of the Bragg mirrors DBR1, DBR2, DBR3 makes it possible to match the optical resonator to a desired wavelength of the light rays L and to set up the fluid sensor component 100 for use for one or more particular types of fluid (for example $CO_2$). A width B2, in a direction parallel to the emission direction R and to the optical axis OA, of the second Bragg mirror DBR2 is, according to the first embodiment, less than widths B1, B3 of the first and/or third Bragg mirror DBR1, DBR3 in the direction parallel to the emission direction R and to the optical axis OA.

The second Bragg mirror DBR2 is bonded with a first surface DBR2-f, facing away from the second substrate 120, onto the second electrical contacts 142, which therefore function as a spacer device 150 between the first and second wafers W1, W2 thereby connected. The cavity 114 remains externally accessible in this case. For the bonding, contact pads (not shown in FIG. 1) may be formed on the surface DBR2-f of the second Bragg mirror DBR2. The second Bragg mirror DBR2 is bonded in such a way that the light rays L traveling along the optical axis OA through the cavity 114 strike the second Bragg mirror DBR2 and are reflected from there in the second percentage counter to the light emission device 112. The light rays L are furthermore transmitted in a further percentage through the second Bragg mirror DBR2. The further percentage is significantly less than the second percentage, and may in particular be the remainder of subtraction of the second percentage from the number one. Dimensions of the cavity 114, in particular a height h of the cavity 114 parallel to the emission direction R, may advantageously be adjusted together with the Bragg mirrors DBR1, DBR2, DBR3 to the wavelength of the light rays L, so that a particularly efficient optical resonator is obtained.

The light rays L transmitted by the second Bragg mirror DBR2 strike the photodiode 116 and cause a voltage drop there, which can be read out from the third electrical contact 144 and the second substrate 120 as a fourth electrical contact 146. To this end, the second substrate is configured to be electrically conductive.

Figure 2A:
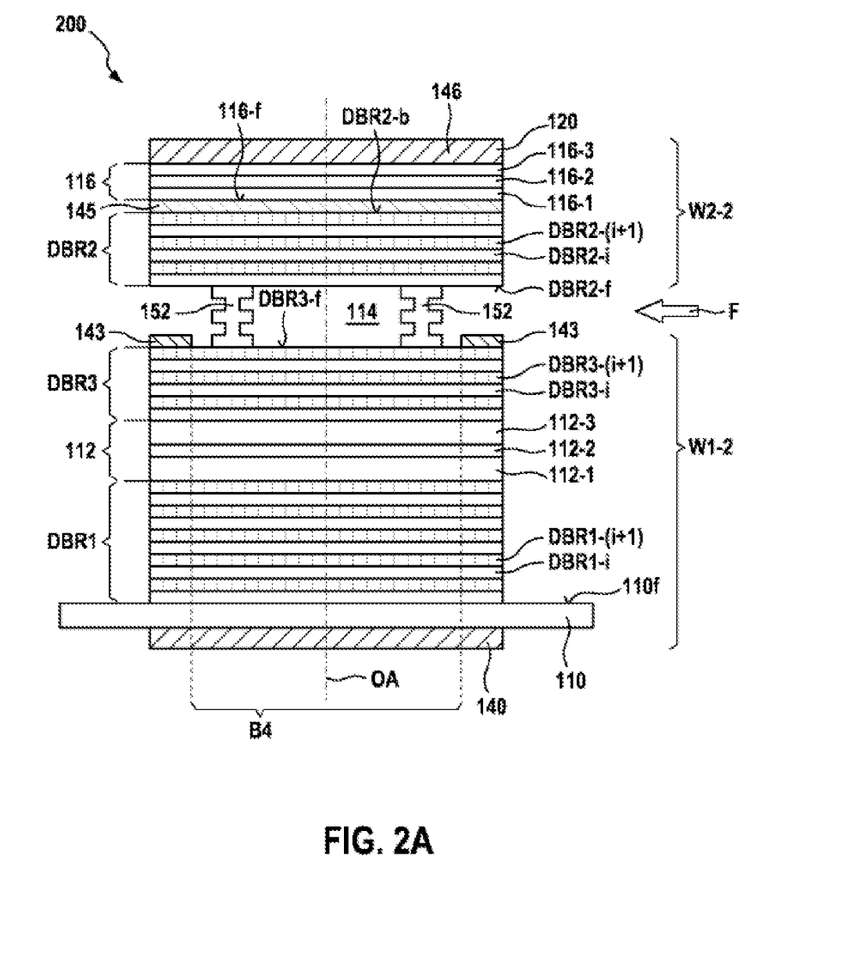
FIG. 2A shows a schematic cross section through a fluid sensor component according to a second embodiment of the present disclosure.

FIG. 2A shows a schematic cross section through a fluid sensor component 200 according to a second embodiment of the present disclosure.

The second embodiment is essentially a variant of the first embodiment. In contrast to the first embodiment, the second embodiment does not comprise a current aperture 118, and the second electrical contact 143 does not function as a spacer device and does not define the cavity 114 either.

Furthermore, the third electrical contact 145 is arranged flat between the second surface 116-f of the photodiode 116 and the second surface DBR2-b of the second Bragg mirror DBR2. The second electrical contact 143 is formed flat on the surface DBR3-f, facing away from the light emission device 112, of the third Bragg mirror DBR3, and in particular leaves a region B4 around the optical axis OAF exposed. The spacer device 152, onto which the second Bragg mirror DBR2 is bonded in order to connect the second wafer W2-2 to the first wafer W1-2, is formed inside the region B4. The second electrical contact 143 is spaced apart from the second Bragg mirror DBR2. The second Bragg mirror DBR2 may therefore also be conductive. Optionally, it may therefore replace the third electrical contact 143.

According to the second embodiment, the spacer device 152 is made by applying and structuring one or more insulating sacrificial layers (for example consisting of an oxide) and in alternation conduction layers (for example consisting of a metal) onto the surface DBR3-f of the third Bragg mirror DBR3. The structuring may be carried out in a comparable way to a metalization process in CMOS processing. The formation of the second electrical contact 143 may advantageously be carried out in the scope of the application of one of the structured metal conduction layers.

For example, the sacrificial layers may be removed after the bonding of the first and second wafers W1-2, W2-2, in the case of the oxide for instance by HF fluid phase etching. Advantageously, the spacer device 152 and/or the second Bragg mirror DBR2 are configured to be nonconductive according to the second embodiment.

The spacer device 152 and the cavity 114 between the second and third Bragg mirrors DBR2, DBR3 are configured in such a way that the light rays L—unimpeded by the spacer device 152—can be passed through the cavity 114 with the fluid F contained therein from the third Bragg mirror DBR3 onto the second Bragg mirror DBR2.

Figure 2B:
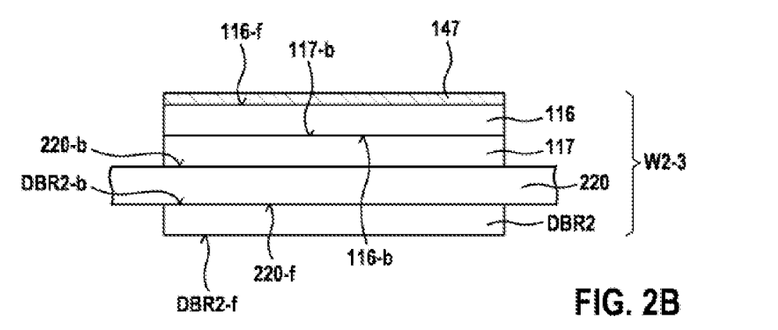
FIG. 2B shows a detail of a schematic cross section through a fluid sensor component according to a third embodiment of the present disclosure.

FIG. 2B shows a detail of a schematic cross section through a fluid sensor component 300 according to a third embodiment of the present disclosure.

The third embodiment is a variant of the second embodiment, from which it differs by the shape and production of the second wafer W2-3, which is shown separately in FIG. 2B.

According to the third embodiment, the second Bragg mirror DBR2 is formed, for example epitaxially grown, at the first surface 220-f of the second substrate 220. A buffer layer 117 is formed on a second surface 220-b of the second substrate 220, which faces away from the first surface 220-f. The photodiode 116 is formed on a surface 117-b of the buffer layer 117 facing away from the second substrate 220, the first surface 116-b of the photodiode 116 bearing on the buffer layer 117. The photodiode 116 is therefore arranged on the surface DBR2-b, facing toward the second substrate 220, of the second Bragg mirror DBR2. The fourth electrical contact 147 is formed, for example vapor-deposited, on the second surface 116-b of the photodiode 116.

According to the third embodiment, the second substrate 220 is essentially transparent for the light rays L. For example, sapphire or $SiO_2$ may be used.

Figure 2C:
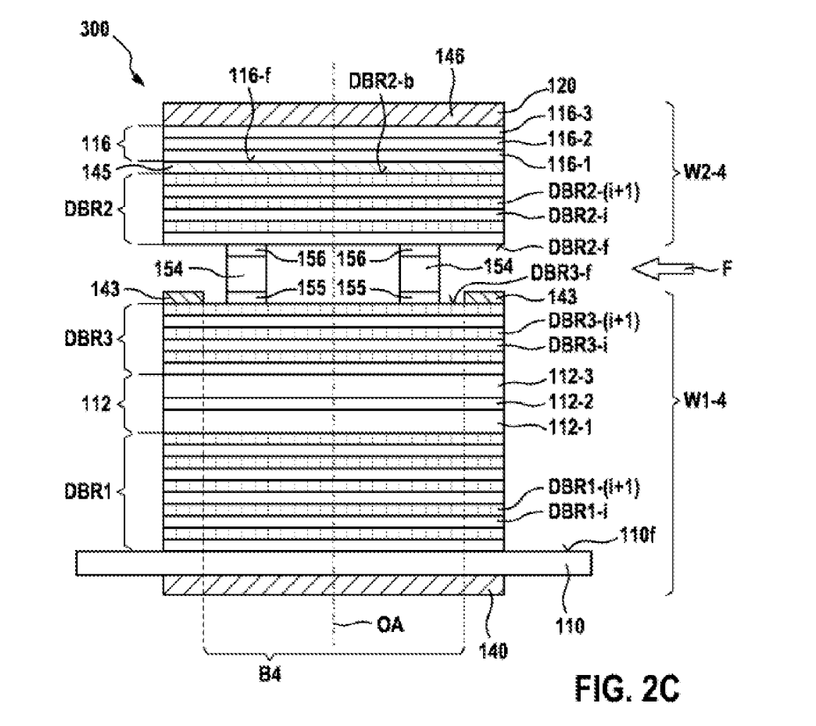
FIG. 2C shows a schematic cross section through a fluid sensor component according to a fourth embodiment of the present disclosure.

FIG. 2C shows a schematic cross section through a fluid sensor component 300 according to a fourth embodiment of the present disclosure.

The fourth embodiment is essentially a variant of the second embodiment according to FIG. 2A, and differs therefrom by the spacer device 154, 155, 156 used. According to the fourth embodiment, the formation of the spacer device 154, 155, 156 is carried out with the steps of:

processing first contact pads 155 on the first wafer W1-4, in particular on the surface DBR3-f, facing away from the light emission device 112, of the third Bragg mirror DBR3;

processing second contact pads 156 on the second wafer W2-4, in particular on the surface DBR2-f, facing away from the second substrate 120, of the second Bragg mirror DBR2;

processing metal columns 154 on the first contact pads 155; and bonding the metal columns 154 to the second contact pads 156 in order to bond the first wafer W1-4 onto the second wafer W2-4.

Figure 3A:
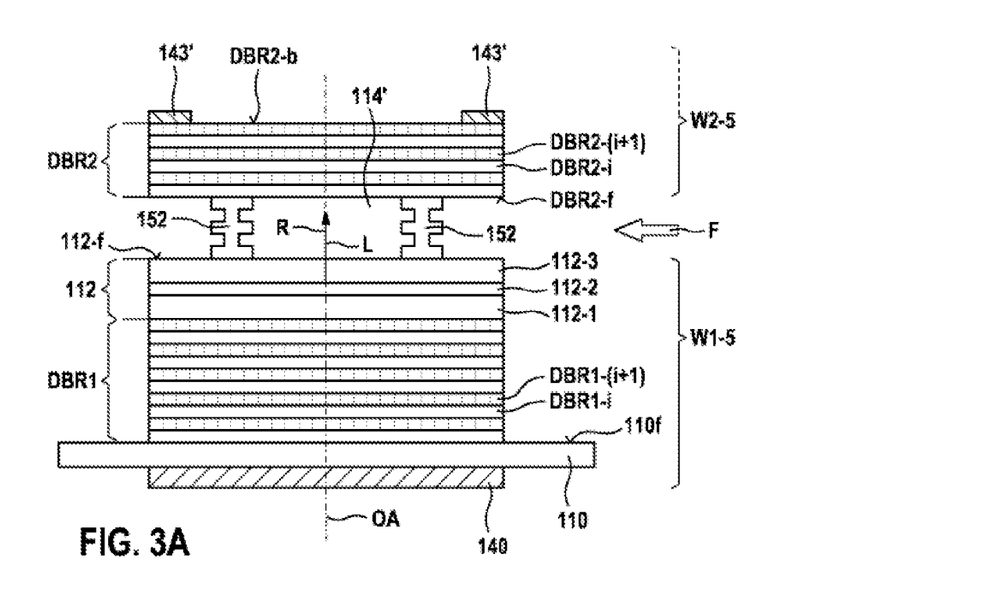
FIG. 3A shows a detail of a schematic cross section through a fluid sensor component according to a fifth embodiment of the present disclosure.

FIG. 3A shows a detail of a schematic cross section through a fluid sensor component according to a fifth embodiment of the present disclosure.

The fifth embodiment is a variant of the first embodiment, from which it differs primarily in that the fifth embodiment does not have a third Bragg mirror DBR3. Furthermore, in the fifth embodiment the second electrical contact 143 also does not function as a spacer device and does not define the cavity 114' either. The fluid sensor component can be less technically elaborate. There is furthermore a modified influence on a wavelength stability of the light rays, and more cycles in the optical resonator through the fluid F are possible, so that the current threshold can be increased.

The construction of the first substrate 110, of the first Bragg mirror DBR1 and of the light emission device 112 is carried out as described in relation to FIG. 1. On the side 112-f, facing away from the first Bragg mirror DBR1, of the light emission device 112, the spacer device 152 for defining the cavity 114', which was described according to FIG. 2A and in relation to the second embodiment, is formed directly.

That is to say, according to the fifth embodiment, the spacer device 152 is made by applying and structuring one or more insulating sacrificial layers (for example consisting of an oxide) and in alternation conduction layers (for example consisting of a metal) onto the surface 112-f of the light emission device 112. The structuring may be carried out in a comparable way to a metalization process in CMOS processing.

The formation of the second electrical contact 143', which is used to supply the light emission device 112 with electrical power, is carried out according to the fifth embodiment not as part of the first wafer W1-5, but as part of the second wafer W2-5, and specifically on the surface DBR2-b, facing toward the second substrate 120 (not shown), of the second Bragg mirror DBR2. Correspondingly, according to the fifth embodiment the spacer device 152 and the second Bragg mirror DBR2 are configured so as to be conductive. A nonconductive layer, over which the third electrical contact 145 used to tap the voltage at the photodiode 116 is connected, for example as described with reference to FIG. 2A, may for example be formed between the second electrical contact 143' and the rest of the second wafer W2-5 (not represented), for example the second substrate 120 and the photodiode 116. Corresponding measures are known to the person skilled in the art.

For example, after the bonding of the first and second wafers W1-5, W2-5, the sacrificial layers may be removed, in the case of the oxide for instance by HF fluid phase etching.

The spacer device 152 and the cavity 114' between the second Bragg mirror DBR2 and the light emission device 112 are configured in such a way that the light rays L—unimpeded by the spacer device 152—can be passed through the cavity 114' with the fluid F contained therein from the third light emission device 112 onto the second Bragg mirror DBR2.

Figure 3B:
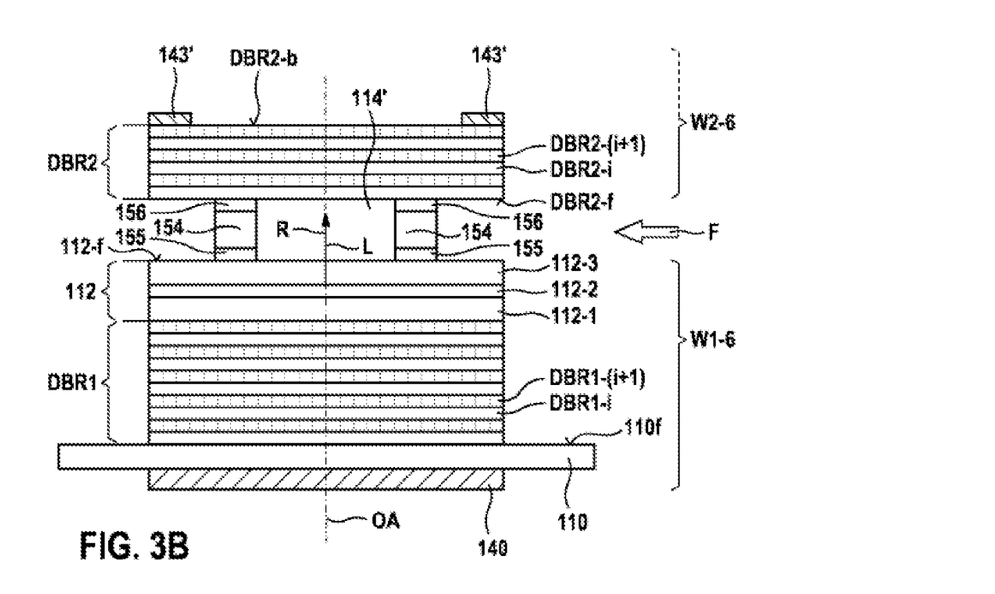
FIG. 3B shows a detail of a schematic cross section through a fluid sensor component according to a sixth embodiment of the present disclosure.

FIG. 3B shows a detail of a schematic cross section through a fluid sensor component according to a sixth embodiment of the present disclosure.

The sixth embodiment is a variant of the fifth embodiment, from which it differs primarily by the shape of the spacer device 154, 155, 156. According to the sixth embodiment, a third Bragg mirror DBR3 is likewise not provided. The configuration of the spacer device 154, 155, 156 is carried out in a similar way to the fourth embodiment, i.e. with the steps of: processing first contact pads 155 on the first wafer W1-6, in particular at the surface 112-f of the light emission device 112 facing away from the first Bragg mirror DBR1;

processing second contact pads 156 on the second wafer W2-6, in particular at the surface DBR2-f of the second Bragg mirror DBR2 facing away from the second substrate 120;

processing metal columns 154 on the first contact pads 155; and bonding the metal columns 154 to the second contact pads 156 in order to bond the first wafer W2-6 to the second wafer W2-6.

According to the sixth embodiment, the spacer device 154, 155, 156 and the second Bragg mirror DBR2 are likewise electrically conductive.

Figure 4:
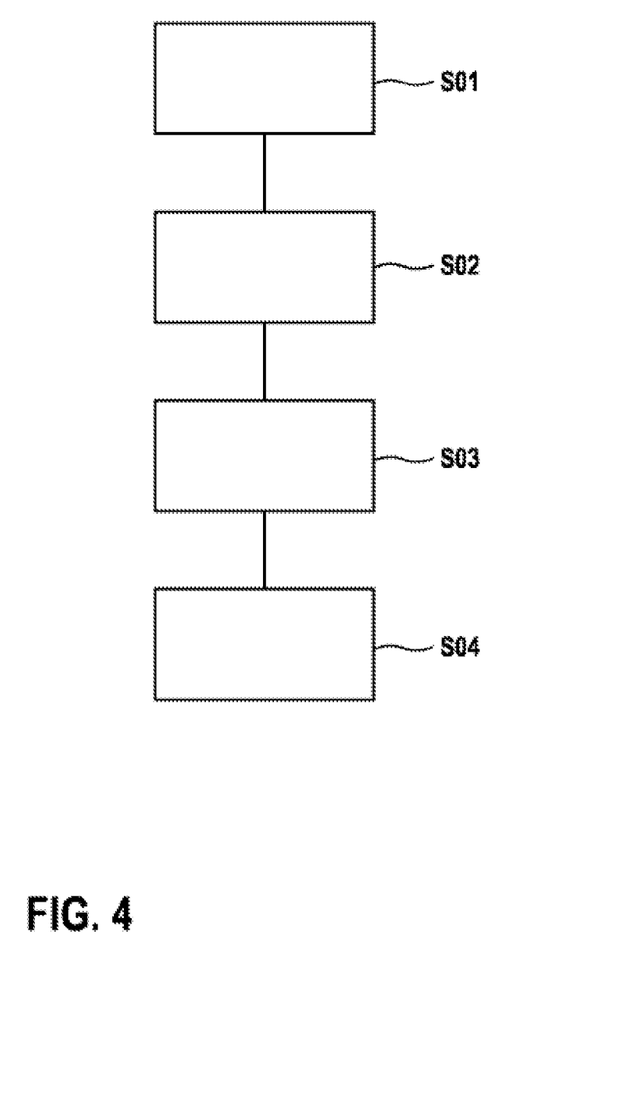
FIG. 4 shows a schematic flowchart to explain a method for producing the fluid sensor component according to the present disclosure.

FIG. 4 shows a schematic flowchart to illustrate a method for producing the fluid sensor component according to the present disclosure. The numbering of the method steps is not intended to specify any particular order, but is used for logical separation. In particular, a plurality of steps may be carried out fully or partially simultaneously.

In a step S01, the first wafer W1; W1-1; W1-2, W1-4; W1-5; W1-6 having the first Bragg mirror DBR1 and the light emission device 112 is formed on the first substrate 110. The light emission device 112 is formed on the first surface DBR1-$f$ of the first Bragg mirror DBR1. The light emission device 112 is configured in order to emit light rays L from the surface 112-$f$, facing away from the first Bragg mirror DBR1, of the light emission device 112 in the emission direction R. The first Bragg mirror DBR1 and the light emission device 112 are formed on the first surface 110-$f$ of the first substrate 110. The emission direction R is perpendicular to the first surface 110-$f$. The light emission device 112 and the first Bragg mirror DBR1 are configured in such a way that the emitted light rays L traveling counter to the emission direction R and striking the first Bragg mirror DBR1 can be reflected in a first percentage in the direction of the emission direction R.

In a step S02, the second wafer W2; W2-1; W2-2, W2-4; W2-5; W2-6 having the second Bragg mirror DBR2 and the photodiode 116 is formed on the second substrate 120; 220, the photodiode 116 being arranged on a surface DBR2-$b$, facing toward the second substrate 120; 220, of the second Bragg mirror DBR2.

In a step S03, the first wafer W1; W1-1; W1-2, W1-4; W1-5; W1-6 is bonded onto the second wafer W2; W2-1; W2-2, W2-3; W2-4; W2-5; W2-6 in such a way that a cavity 114, 114', into which a fluid F can be introduced and which can be passed through by the light rays L, is formed on the side 112-$f$, facing away from the first Bragg mirror DBR1, of the light emission device 112 and on the surface DBR2-$f$, facing away from the photodiode 116, of the second Bragg mirror DBR2.

The light emission device 112 and the second Bragg mirror DBR2 are configured and arranged in such a way that the emitted light rays L traveling in the direction of the emission direction R and striking the second Bragg mirror DBR2 can be reflected in the second percentage counter to the emission direction R and can be transmitted in the further percentage.

The photodiode 116 is configured and arranged in such a way that at least some of the light rays L strike the photodiode 116, after passing through the cavity 114; 114' and after the transmission of the light rays L through the second Bragg mirror DBR2.

In a step S04, the fluid sensor component is divided up from the first and second wafers W1; W1-1; W1-2, W1-4; W1-5; W1-6, W2; W2-1; W2-2; W2-3; W2-4; W2-5; W2-6.

Figure 5A:
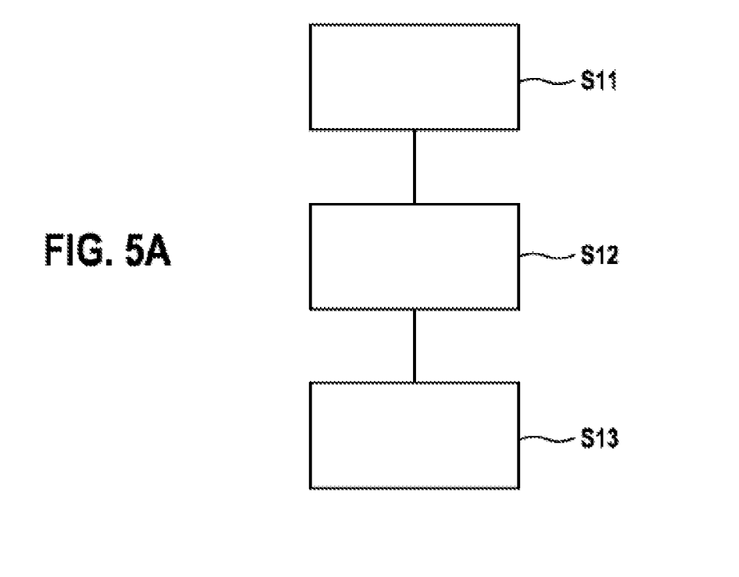
FIG. 5A shows a schematic flowchart to explain a method for detecting a fluid according to a further aspect of the present disclosure by means of an integrated micromechanical fluid sensor component according to the disclosure.

FIG. 5A shows a schematic flowchart to explain a method for detecting a fluid according to a further aspect of the present disclosure by means of an integrated micromechanical fluid sensor component according to the disclosure. In this case, reference is also made to FIG. 5B.

Figure 5B:
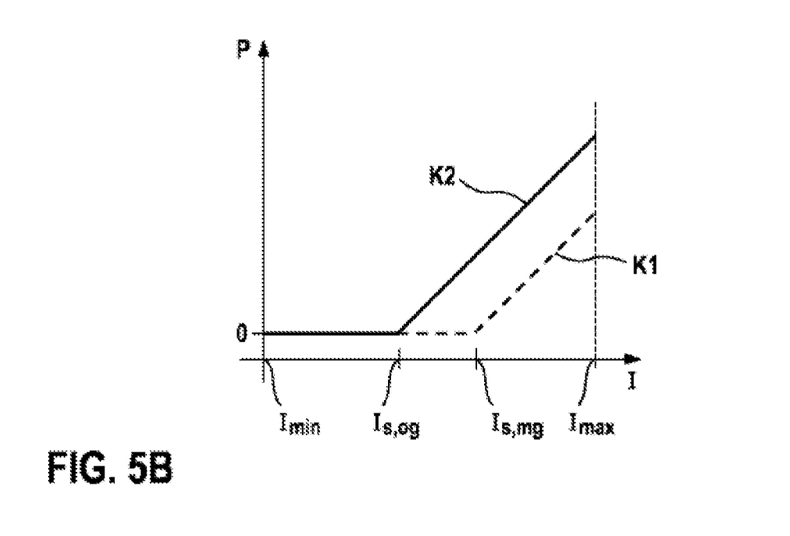
FIG. 5B shows a schematic graph to explain the method for detecting the fluid according to the further aspect of the present disclosure.

FIG. 5B shows a schematic graph to explain the method for detecting the fluid according to the further aspect of the present disclosure.

In a step S11, while the fluid F is in the cavity 114, a first P-I characteristic curve K1 is recorded. In this case, the current I is a current with which the light emission device 112 is supplied in order to emit the light rays L, for example via the first and second electrical contacts 140, 142, 143, 143'. In order to record the first P-I characteristic curve, the current is varied in particular between a minimum current value $I_{min}$ and a maximum current value $I_{max}$, for example continuously, in particular monotonically or strictly monotonically, increased or decreased. The variation may also be carried out discontinuously with discrete current values. The minimum current value $I_{min}$ may also be zero mA.

The power P is a power which is formed on the photodiode 116 in response to the light rays L striking the photodiode 116 on the photodiode 116 and is read out from the photodiode 116, for instance as a voltage, for example via the third and fourth electrical contacts 144, 145, 146, 147.

In a step S12, a first threshold current $I_{s,mg}$ is determined, which is a value of the current I at which the power P on the photodiode 116 assumes a finite value according to the first P-I characteristic curve.

In a step S13, the determined first threshold current $I_{s,mg}$ is compared with a predetermined reference threshold current $I_{s,og}$ in order to detect the fluid F. According to the embodiment described with reference to FIG. 5A, the predetermined reference threshold current $I_{s,og}$ is a second threshold current according to a second P-I characteristic curve K2. The second P-I characteristic curve K2 is recorded in an essentially similar way to the first characteristic curve K1, but in contrast to the first P-I characteristic curve K1 while the fluid F is not contained in the cavity 114; 114'. For example, the second P-I characteristic curve K2 may be recorded while a vacuum is provided in the cavity 114; 114'.

The comparison in step S13 may, for example, be carried out by an electronic drive apparatus connected to the fluid sensor component according to the disclosure.

As an alternative, a reference fluid determined as a function of the fluid to be detected may be provided in the cavity 114; 114'. If, for instance, human exhaled air is to be detected as the fluid f, the intention being in particular to determine a molecular concentration of alcohol molecules in the exhaled air, the second P-I characteristic curve K2 may be recorded while average human exhaled air is contained as a reference fluid in the cavity 114; 114'. By communication or coordination with a weather station, optionally improved information about the reference fluid may be received.

If the light emission device 112 is operated continuously, for instance over a plurality of μs, a temperature in the integrated micromechanical fluid sensor component according to the disclosure, particularly in the optical resonator, may increase. A wavelength of the light rays L emitted by the light emission device 112 may thereby be shifted. Advantageously, the light emission device 112 is operated in short-pulsed operation. As an alternative, the light emission device 112 can also be operated in the stabilized state, since the temperature generated in the optical resonator depends only slightly on the ambient temperature. If the fluid sensor component is used in other equipment, a heat sink already present therein may also be used in order to keep the effect of the ambient temperature low.

A shift in the wavelength of the emitted light rays L due to the described temperature effects may also be used intentionally in order to modify the wavelength over a desired range. This may be advantageous when, for instance, a gas which has a particularly narrow absorption peak is to be detected. To this end, reading out of the voltage U from the photodiode 116 may be carried out while the fluid sensor component is being constantly heated because of continuous operation of the light emission device 112.

Although the present disclosure has been described above with the aid of preferred exemplary embodiments, it is not restricted thereto but may be variously modified. In particular, the disclosure may be varied or modified in a variety of ways without departing from the core of the disclosure.

For example, a spacer device may also be produced by applying at least one spacer onto the first or second wafer. The spacer may either be applied in an already thinned form with the aid of a carrying structure, for example a carrying wafer, or may be thinned back after application. The material of the spacer may for example be or comprise Si, which is structured in the form of a frame having a plurality of through-channels. The bonding between the first and second wafers is carried out, for example, by activated direct Si bonding, for example on oxide layers which are present in a structured form on the surface of the first and second wafers. The structuring of the through-channels may also be carried out after the bonding processing.

A spacer device may also be produced by columns, onto which the respective other wafer is bonded, being grown on the first or second wafer in addition to the parts configured as a mesa.

The contacting of the photodiode may also—instead of for instance between the second Bragg mirror and the photodiode—be carried out on the surface of the second Bragg mirror facing away from the second substrate, this mirror being configured to be conductive.

If a required sensitivity of the fluid sensor component is very low, it may also be formed without an external cavity. During the wafer mounting, an etalon effect of the cavity may be used for wave adjustment.

It is also possible to introduce a filter. In this case, the wide gain spectrum of the surface emitter may be used—even below the threshold, and a relevant wavelength may be filtered out by the filter.

Further layers may advantageously be formed on, in particular at, a surface of the second Bragg reflector facing toward the cavity. For example, it is possible to form an antireflection protection layer which is preferably tuned to a wavelength at which an analyte of the fluid or in the fluid has the greatest absorption cross section. Furthermore, a—maximally passive—adsorption protection layer may be formed on a surface exposed to the fluid. By inert materials, it is possible to achieve a particularly low adsorption enthalpy with particular molecular species. Furthermore, it is possible to provide an optical aperture in order to spatially limit the path of the light rays.

By means of the structure of the fluid sensor component, in particular the heights of the individual layers and the materials used, in particular the semiconductor material systems, the fluid sensor component may be adjusted sensitively for different fluids, for instance $CO_2$, $NO_x$, $O_3$.

The Bragg mirrors may be optimized for different applications, for instance by varying the number of pairs of layers with a different refractive index. In this case, for example, optimization may be carried out with a view to a low current threshold, a high sensitivity, a stable wavelength or a design which is technically not very elaborate.

Some layers or elements, for example of the second Bragg mirror, may also be configured to be wider than schematically represented in the figures, for example with dimensions which correspond to the footprint of the fluid sensor component, or greater than this.

The photodiode and/or the second wafer may be configured and arranged in such a way that at least some of the light rays of a plurality of light emission devices and/or a plurality of surface emitters of the first wafer strike the photodiode. In this case, the fluid sensor component comprises a plurality of mesas. In this way, a measurement accuracy can be increased since it is possible to average over a plurality of cavities and scale the path of the light rays through the fluid with the number of mesas.

In order to detect the fluid, the light emission device 112 may as an alternative be supplied with a constant current I by the drive apparatus in the presence of the fluid F in the cavity 114; 114', while a voltage U generated at the photodiode 116 is evaluated.

A further variant consists in evaluating, by means of the drive apparatus, the current I which is required in the presence of the fluid F in the cavity 114; 114' in order to reach a predetermined voltage U at the photodiode 116.

The invention claimed is:

1. A method for producing an integrated micromechanical fluid sensor component, comprising:
    forming a first wafer having a first Bragg mirror and a light emission device on a first substrate, the light emission device configured to emit light rays from a surface, facing away from the first Bragg mirror, of the light emission device in an emission direction, wherein:
        the first Bragg mirror and the light emission device are formed on a first surface of the first substrate,
        the emission direction is perpendicular to the first surface, and
        the light emission device and the first Bragg mirror are configured such that emitted light rays traveling counter to the emission direction and striking the first Bragg mirror are configured to be reflected in a first percentage in the direction of the emission direction;
    forming a second wafer having a second Bragg mirror and a photodiode on a second substrate, the photodiode arranged on a surface, facing toward the second substrate, of the second Bragg mirror;
    bonding or adhesively bonding the first wafer onto the second wafer by a spacer device such that, on the side, facing away from the first Bragg mirror, of the light emission device and on a surface, facing away from the photodiode, of the second Bragg mirror, a cavity defined by the spacer device, into which a fluid is configured to be introduced and which is configured to be passed through by the light rays, is formed, wherein:
        the light emission device and the second Bragg mirror are configured and arranged such that the emitted light rays traveling in the direction of the emission direction and striking the second Bragg mirror are configured to be reflected in a second percentage counter to the emission direction and are configured to be transmitted in a further percentage, and
        the photodiode is configured and arranged such that at least some of the light rays strike the photodiode, after passing through the cavity and after transmission of the light rays through the second Bragg mirror;
    forming a third Bragg mirror as a constituent of the first wafer on the surface, facing away from the first Bragg mirror, of the light emission device, the light emission device and the third Bragg mirror configured such that the emitted light rays traveling in the direction of the emission direction and striking the third Bragg mirror are configured to be reflected in a third percentage counter to the emission direction and are configured to be transmitted in yet another percentage; and
    dividing up the fluid sensor component from the first and second wafers.

2. The method as claimed in claim 1, wherein the first Bragg mirror is arranged between the first substrate and the light emission device.

3. The method as claimed in claim 2, wherein the spacer device is formed by:
processing first contact pads on the first wafer;
processing second contact pads on the second wafer;
processing metal columns on the first or second contact pads; and
bonding the metal columns to the second or first contact pads in order to bond the first wafer onto the second wafer.

4. The method as claimed in claim 2, wherein the spacer device is formed by:
applying a sacrificial layer onto the first or second wafer;
structuring the sacrificial layer;
applying a conductive layer;
structuring the conductive layer; and
removing the sacrificial layer after the bonding or adhesive bonding of the second wafer onto the first wafer by the spacer device.

5. The method as claimed in claim 1, wherein the photodiode is arranged between the second substrate and the second Bragg reflector.

6. The method as claimed in claim 1, wherein the second substrate is a substrate that is essentially transparent for the light rays and arranged between the second Bragg reflector and the photodiode.

7. An integrated micromechanical fluid sensor component, comprising:
a first wafer having a first Bragg mirror and a light emission device on a first substrate, the light emission device configured to emit light rays from a surface, facing away from the first Bragg mirror, of the light emission device in an emission direction, wherein:
the first Bragg mirror and the light emission device are formed on a first surface of the first substrate,
the emission direction is perpendicular to the first surface, and
the light rays and the first Bragg mirror are configured such that light rays traveling counter to the emission direction and striking the first Bragg mirror are configured to be reflected in a first percentage in the direction of the emission direction;
a second wafer having a second Bragg mirror and a photodiode on a second substrate, the photodiode arranged on a surface, facing toward the second substrate, of the second Bragg mirror, wherein:
the first wafer is bonded or adhesively bonded onto the second wafer by a spacer device such that, on a side, facing away from the first Bragg mirror, of the light emission device and on a surface, facing away from the photodiode, of the second Bragg mirror, a cavity defined by the spacer device, into which a fluid is configured to be introduced and which is configured to be passed through by the light rays, is formed,
the light emission device and the second Bragg mirror are configured and arranged such that the emitted light rays traveling in the direction of the emission direction and striking the second Bragg mirror are configured to be reflected in a second percentage counter to the emission direction and are configured to be transmitted in a further percentage, and
the photodiode is configured and arranged such that at least some of the light rays strike the photodiode, after passing through the cavity and after transmission of the light rays through the second Bragg mirror; and
a third Bragg mirror as a constituent of the first wafer on the surface, facing away from the first Bragg mirror, of the light emission device, the light emission device and the third Bragg mirror configured such that the emitted light rays traveling in the direction of the emission direction and striking the third Bragg mirror are configured to be reflected in a third percentage counter to the emission direction and are configured to be transmitted in yet another percentage.

8. A method for detecting a fluid by an integrated micromechanical fluid sensor component including (i) a first wafer having a first Bragg mirror and a light emission device on a first substrate, the light emission device configured to emit light rays from a surface, facing away from the first Bragg mirror, of the light emission device in an emission direction, wherein the first Bragg mirror and the light emission device are formed on a first surface of the first substrate, wherein the emission direction is perpendicular to the first surface, and wherein the light rays and the first Bragg mirror are configured such that light rays traveling counter to the emission direction and striking the first Bragg mirror are configured to be reflected in a first percentage in the direction of the emission direction, (ii) a second wafer having a second Bragg mirror and a photodiode on a second substrate, the photodiode arranged on a surface, facing toward the second substrate, of the second Bragg mirror, wherein the first wafer is bonded or adhesively bonded onto the second wafer by a spacer device such that, on a side, facing away from the first Bragg mirror, of the light emission device and on a surface, facing away from the photodiode, of the second Bragg mirror, a cavity defined by the spacer device, into which a fluid is configured to be introduced and which is configured to be passed through by the light rays, is formed, wherein the light emission device and the second Bragg mirror are configured and arranged such that the emitted light rays traveling in the direction of the emission direction and striking the second Bragg mirror are configured to be reflected in a second percentage counter to the emission direction and are configured to be transmitted in a further percentage, and wherein the photodiode is configured and arranged such that at least some of the light rays strike the photodiode, after passing through the cavity and after transmission of the light rays through the second Bragg mirror; and (iii) a third Bragg mirror as a constituent of the first wafer on the surface, facing away from the first Bragg mirror, of the light emission device, the light emission device and the third Bragg mirror configured such that the emitted light rays traveling in the direction of the emission direction and striking the third Bragg mirror are configured to be reflected in a third percentage counter to the emission direction and are configured to be transmitted in yet another percentage, the method comprising:
recording a P-I characteristic curve while the fluid is in the cavity, a current being a current with which the light emission device is supplied in order to emit the light rays, and a power P being a power which is formed on the photodiode in response to the light rays striking the photodiode on the photodiode and is read out from the photodiode;
determining a threshold current, which is a value of the current at which the power on the photodiode assumes a finite value according to the P-I characteristic curve;

comparing the determined threshold current with a predetermined reference threshold current for detection of the fluid.

\* \* \* \* \*